United States Patent [19]
Williams

[11] Patent Number: 4,904,238
[45] Date of Patent: Feb. 27, 1990

[54] IRRIGATION/ASPIRATION HANDPIECE

[75] Inventor: Rodger W. Williams, Arlington, Tex.

[73] Assignee: Alcon Laboratories, Inc., Fort Worth, Tex.

[21] Appl. No.: 135,730

[22] Filed: Dec. 21, 1987

[51] Int. Cl.$^4$ .............................................. A61M 7/00
[52] U.S. Cl. ...................................... 604/43; 604/35; 604/39; 604/264; 604/283
[58] Field of Search .................... 604/22, 27, 35, 39, 604/43, 44, 45, 264, 272, 280, 283, 4–6; 128/305; 138/89, 112; 24/115 G; 285/178; 403/350

[56] References Cited

U.S. PATENT DOCUMENTS

| | | | |
|---|---|---|---|
| 3,765,420 | 10/1973 | Felczak | 604/180 |
| 3,889,046 | 6/1975 | Oberdier | 285/178 |
| 3,929,126 | 12/1975 | Corsaut | 604/43 |
| 3,994,297 | 11/1976 | Kopf . | |
| 4,011,869 | 3/1977 | Seiler, Jr. | 128/305 |
| 4,069,814 | 1/1978 | Clemens . | |
| 4,294,251 | 10/1981 | Greenwald et al. . | |
| 4,316,465 | 2/1982 | Dotson, Jr. | 128/276 |
| 4,377,897 | 3/1983 | Eichenbaum et al. | 604/272 |
| 4,382,618 | 5/1983 | Grisebach | 285/178 |
| 4,428,748 | 1/1984 | Peyman et al. | 604/22 |
| 4,493,696 | 1/1985 | Uldall | 604/43 |
| 4,548,597 | 10/1985 | Nelson | 604/43 |
| 4,553,957 | 11/1985 | Williams et al. | 604/43 |
| 4,578,059 | 3/1986 | Fabricant et al. | 604/43 |
| 4,652,255 | 3/1987 | Martinez | 604/43 |

FOREIGN PATENT DOCUMENTS

0621834 6/1961 Canada ................................. 138/112

Primary Examiner—C. Fred Rosenbaum
Assistant Examiner—Adam J. Cermak
Attorney, Agent, or Firm—Zarley, McKee, Thomte, Voorhees & Sease

[57] ABSTRACT

A hand-held cannula assembly for irrigating and aspirating opthalmic surgical sites includes as irrigation cannula circumscribed about an aspiration cannula and extending out through the forward end of the assembly from a reservoir for the irrigation fluid in the handle. Pressurized irrigation fluid is supplied to the reservoir through the rearward end of the handle and flows through openings in the irrigation cannula periphery into an annular flow passage between the two cannulas. An opening in the irrigation cannula issues the irrigation fluid at the surgical site. Aspiration fluid is drawn into the aspiration cannula which extends through the handle interior to an outflow opening at the rearward handle end. The irrigation/aspiration tip exterior is made to be smooth, protrusionless, unitary and one-piece in design to afford a minimum in tissue tearing at the surgical site, while also allowing improved irrigation fluid flow a the site.

30 Claims, 3 Drawing Sheets

IRRIGATION/ASPIRATION HANDPIECE

BACKGROUND OF THE INVENTION

1. Field of the Invention

The present invention relates to a surgical instrument, and in particular, to an irrigation/aspiration handpiece.

2. Problems in the Art

Some surgical procedures require simultaneous irrigation and aspiration at the surgical site. One method of accomplishing this would be to operate separate aspiration and irrigation tools at the site. This is especially problematic for small or delicate surgery, for example, in microsurgery.

Combination irrigation/aspiration handpieces have therefore been developed. One useful handpiece is disclosed in U.S. Pat. No. 4,553,957 by inventors Rodger W. Williams and Charles W. Atwood, which is incorporated by reference herein. That patent discloses a handpiece having a hollow interior section used for an irrigation fluid reservoir, and an aspiration cannula extending from an aspiration connection all the way to the end of the surgical tip, through the irrigation fluid reservoir. A second cannula surrounding the aspiration cannula communicates with the fluid reservoir and directs irrigation fluid to the surgical site. A handpiece of this type requires that the irrigation and aspiration cannulas, being of two separate pieces, be secured to one another. Additionally, handpieces of this type are conventional in that irrigation ports from the irrigation cannula are disposed at opposite sides towards the distal end of the irrigation cannula with the position of the aspiration port of the aspiration cannula extending forward of the irrigation ports and being intermediate between the position of the irrigation ports.

There is also a need for a secure and sealing connection so that there is no inter-mixing of the irrigation fluids with the aspiration lines and materials. It is therefore critical that connecting conduits between the irrigation/aspiration sources and the handpiece are secure, reliable, and not subject to deterioration or break down because of strain or loosening.

It is therefore a primary object of the present invention to present an irrigation/aspiration handpiece which improves over or solves the problems and deficiencies in the art.

Another object of the present invention is to provide an irrigation/aspiration handpiece which is accurate, reliable, and simultaneously provides irrigation and aspiration to a surgical site.

A further object of the present invention is to provide an irrigation/aspiration handpiece which does not have exposed, interrupted joints or connecting pieces, and which does not have any edges which are likely to catch or cause tears at the surgical site.

Another object of the present invention is to provide an irrigation/aspiration handpiece which has a surgical tip which has smooth, unitary, uninterrupted surfaces.

A further object of the present invention is to provide an irrigation/aspiration handpiece which has improved irrigation properties without affecting aspiration.

Another object of the present invention is to provide an irrigation/aspiration handpiece which provides minimal strain on conduits between irrigation and aspiration sources and the handpiece.

Another object of the present invention is to provide an irrigation and aspiration handpiece which is efficient, economical, and durable in construction, maintenance and use.

These and other objects, features, and advantages of the present invention will become apparent with reference to the accompanying specification and claims.

SUMMARY OF THE INVENTION

The present invention includes an improved apparatus for irrigating (supplying fluid to) and aspirating (withdrawing fluid from) a surgical site; otherwise called an irrigation/aspiration handpiece. An elongated handle encapsulates separate conduits for irrigation fluid and aspiration. These conduits are connected to irrigation and aspiration sources and enter the proximal end of the handle and proceed through the handle's intermediate body section towards the opposite, distal end of the handle. A nose chamber is positioned in the distal end of the handle, and includes a hollow interior comprising a reservoir for irrigation fluid. The reservoir of the nose chamber is therefore in direct fluid communication with the irrigation fluid conduit.

A surgical tip having a narrow, generally tubular solid housing, is positioned on the distal end of the nose chamber and extends outwardly from the handle. The surgical tip also has a hollow interior section which is itself in direct communication with the reservoir of the nose chamber. Near the distal end of the surgical tip which is tapered and closed, are one or more irrigation outlet openings or ports which are in communication with the hollow interior of the surgical tip. Irrigation fluid therefore communicates from the irrigation conduit through the reservoir of the nose chamber and through the hollow interior of the surgical tip out of the irrigation ports to the exterior of the tip.

The surgical tip also includes an aspiration inlet opening or port between the very distal end of the surgical tip and the aspiration ports. An aspiration cannula extends from the aspiration inlet port through the hollow interior of the surgical tip and through the reservoir of the nose chamber and then is directly put in fluid communication with the aspiration conduit.

The handpiece therefore provides for simultaneous irrigation and aspiration at a surgical site. The surgical tip is unitary, and has uninterrupted surfaces. The edges of the irrigation/ aspiration ports can be rounded to reduce any chance for catching or tearing at the surgical site. The irrigation and aspiration systems are entirely sealed from one another in the handpiece, and the positioning of the aspiration port with respect to the irrigation ports allows sufficient irrigation without obstructing the aspiration capabilities of the handpiece.

In a particular embodiment of the surgical tip, the irrigation ports are radially disposed around the perimeter of the distal end of the surgical tip with the aspiration port being positioned slightly ahead of the irrigation ports on the side of the distal end of the surgical tip. Solid portions of the tip housing separate the irrigation ports. The solid portions are impermeable to fluids. The plurality of irrigation ports provides increased and more beneficial irrigation flow to the surgical site. The irrigation ports can be distributed so that a port-free solid portion of the tip housing between irrigation ports is provided immediately adjacent and proximally to the aspiration port to insure that the irrigation fluid, under pressure, does not disrupt the aspiration capabilities of the handpiece.

Because the aspiration and irrigation conduits extend from outside of the handpiece through the intermediate body section of the handpiece, a strain relief is incorporated into the proximal end of the handpiece. The strain relief consists of an end plug having two apertures to receive both conduits side by side. A strain plug is then positioned interiorly of the end plug and also has two apertures to receive the conduits side by side. However, the two apertures in the strain plug are offset from the apertures in the end plug by rotating the apertures in the strain plug slightly to provide a bending in the aspiration and irrigation conduits. This provides necessary strain relief and assists in securing the conduits in place.

DETAILED DESCRIPTION OF THE PREFERRED EMBODIMENT

Figures 1, 2, 4, 5A, 6A:
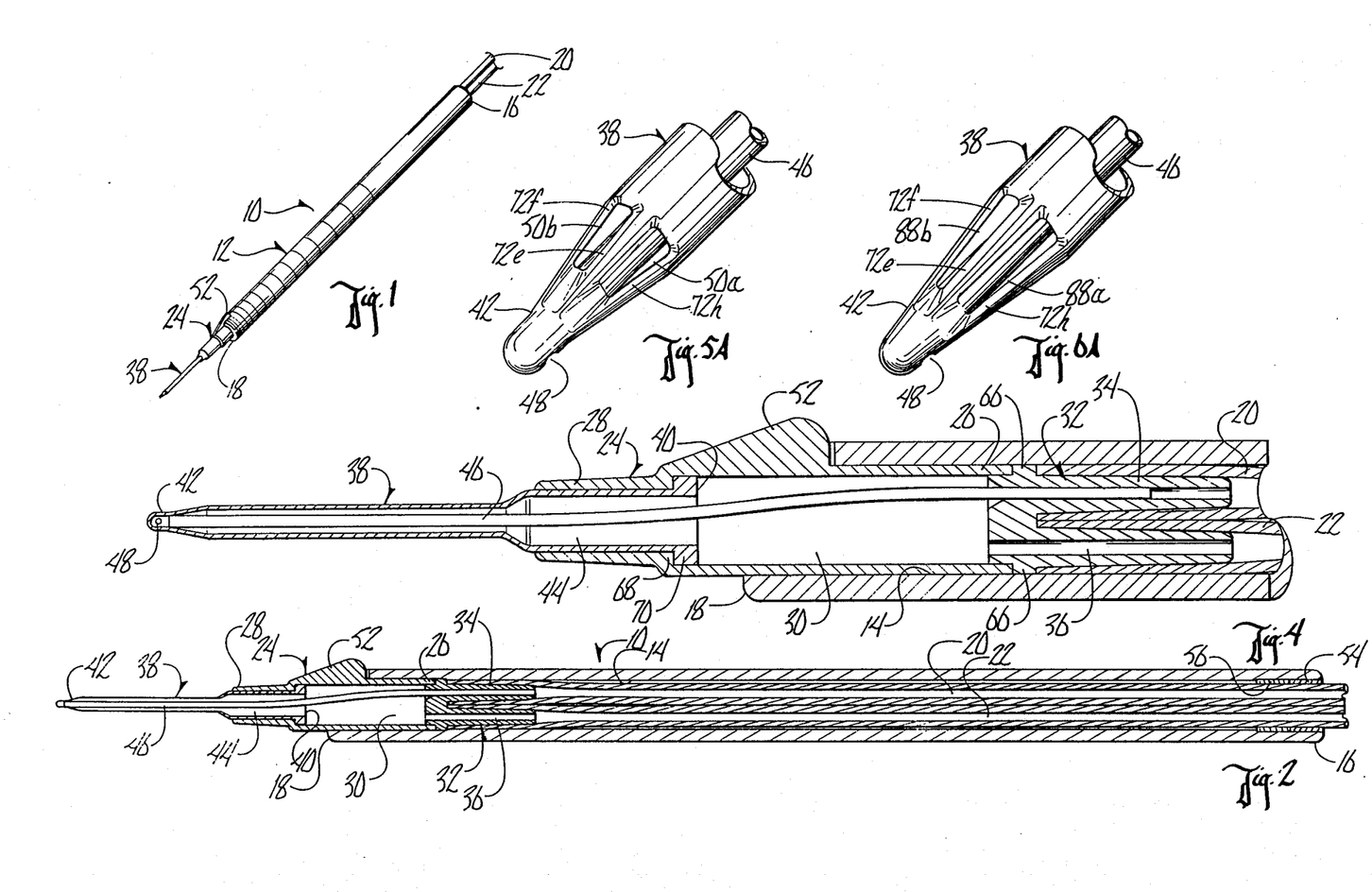
FIG. 1 is a perspective view of an embodiment of an irrigation/aspiration handpiece according to the present invention.
FIG. 2 is a longitudinal sectional view of the handpiece of FIG. 1.
FIG. 4 is an enlarged partial sectional view according to FIG. 2.
FIG. 5A is a partial perspective view of the tip of the handpiece of FIG. 1.
FIG. 6A is a partial perspective view of alternative embodiment of a tip for a handpiece according to the invention.
Figures 3, 7, 8:
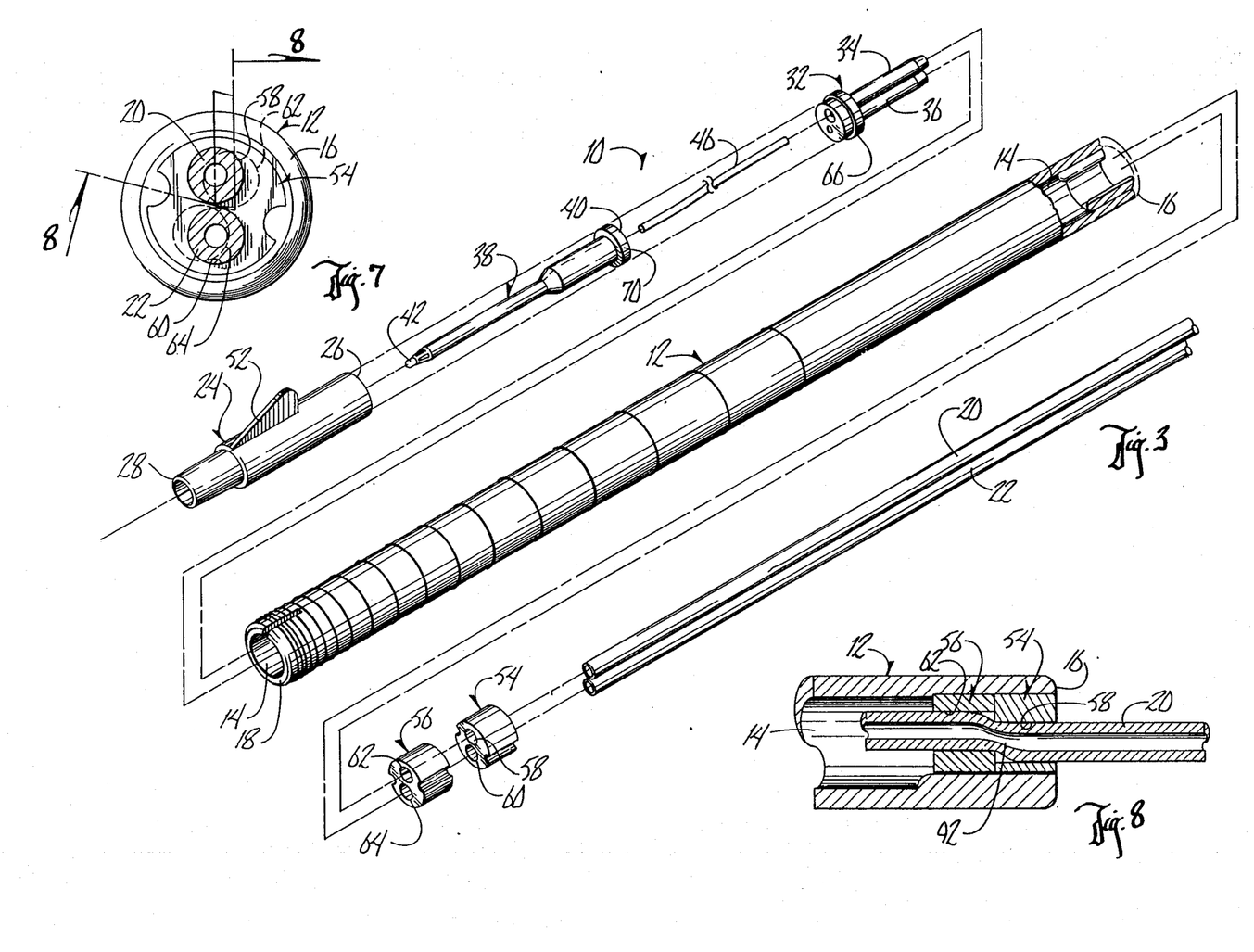
FIG. 3 is an exploded view of the handpiece of FIG. 1.
FIG. 7 is a proximal end view of the handpiece of FIG. 1 with offset strain relief members shown in broken lines.
FIG. 8 is a partial sectional top view taken along lines 8—8 of FIG. 7.

With reference to the drawings, and particularly FIGS. 1-3, there is shown an improved apparatus for irrigating (supplying fluid to) and aspirating (withdrawing fluid from) a surgical site; which for purposes of this description will be referred to as an irrigation/aspiration handpiece 10. The handle 12 of handpiece 10 is an elongated body which in the preferred embodiment has a hollow center bore 14 and an open proximal end 16 and open distal end 18. The terms "distal" and "proximal" relate to the relationship of the opposite ends 18 and 16 of handpiece 10 with the conduits to sources of aspiration and irrigation.

An aspiration conduit 20 enters the proximal end 16 of handle 12 from an aspiration source (not shown), while similarly an irrigation conduit 22 enters the proximal end 16 of handle 12 from an irrigation source (not shown).

A nose chamber 24 is positioned in association with the distal end 18 of handle 12 having its proximal end 26, in the preferred embodiment, sealingly fitted within distal end 18 of handle 12, and having a distal end 28 extending outwardly therefrom. Nose chamber 24 has a hollow interior portion which comprises a reservoir 30 for irrigation fluid. The distal end 28 of nose chamber 24 is open whereas the proximal end 26 contains chamber bulkhead 32, which comprises a first connection 34 to which is attached in fluid communication aspiration conduit 20, and a second connection 36 which is attached in fluid communication to irrigation conduit 22. Second connection 36 is in turn in fluid communication with reservoir 30.

A surgical tip 38 having a narrow, generally tubular solid housing, is secured in association with distal end 28 of nose chamber 24 at its proximal end 40, and extends to its distal end 42 which is tapered and closed. Surgical tip 38 also has hollow interior 44.

An aspiration cannula 46 extends from first connection 34 of chamber bulkhead 32, through reservoir 30 and through hollow interior 44 of surgical tip 38 to near the very distal end 42 of surgical tip 38. Aspiration cannula 46 forms a separate and sealed fluid communication line between aspiration conduit 20 and the distal end 42 of surgical tip 38.

By brief reference to FIGS. 4 and 5A-E, it can be seen that the solid housing of the distal end 42 of surgical tip 38 contains an aspiration port 48 which is in fluid communication with aspiration cannula 46, and also contains a plurality of irrigation ports 50a, b, c, and d, which are in fluid communication with hollow interior 44 of surgical tip 38, which in turn is in fluid communication with reservoir 30 of nose chamber 24, which in turn is in fluid communication with irrigation conduit 22. The irrigation ports 50a, b, c, and d are separated by solid portions 72e, f, g, and h of the solid housing of tip 38. It can therefore be seen that handpiece 10 allows simultaneous irrigation and aspiration at the surgical site.

Also shown in FIGS. 1-4 is a raised indicia member 52 in the form of a fin at the distal end 18 of handle 12, which gives a visual and tactile indicator of the position of the aspiration port 48. For example, in the embodiment of FIG. 1 and 4, aspiration port 48 is positioned on the side of surgical tip 38, whereas raised indicia member 52 is on the top of handpiece 10. With this relationship, a surgeon can always and quickly determine the location of the aspiration port 48.

FIG. 2 shows that aspiration and irrigation conduits 20 and 22 pass through the proximal end 16 of handle 12, and are held in position by end plug 54 and strain plug 56. As can be seen in FIGS. 3 and 7, end plug 54 has two adjacent apertures 58 and 60, whereas strain plug 56 has adjacent apertures 62 and 64 (shown in broken lines in FIG. 7), all of which receive conduits 20 and 22 without constriction to fluid flow therethrough. The apertures 58, 60, 62 and 64, of end and strain plugs 54 and 56 can frictionally restrict and assist in securing conduits 20 and 22.

It can also be seen that in the preferred embodiment, the interior perimeter wall of the hollow center defined by bore 14 is frictionally abutted by a shoulder 66 of chamber bulkhead 32, and that first and second connections 34 and 36 can comprise connecting nipples for tubular aspiration and irrigation conduits 20 and 22. Aspiration cannula 46 can frictionally fit within the first connection 34, whereas the opposite end of irrigation cannula 46 can frictionally fit down into the distal end 42 of surgical tip 38 (see in particular, for example, FIGS. 5C and 6C).

FIGS. 2 and 4 also show that distal end 28 of nose chamber 24 narrows from its proximal end 26. Shoulder 68 is formed interiorly which prevents flange 70 of surgical tip 38 from moving forward when in position. The distal end 42 of surgical tip 38 itself narrows from proximal end 40 to present the narrow, unitary, uninterrupted surface for surgical tip 38 to be inserted into the surgical incision or otherwise used in surgery.

FIG. 3 depicts in exploded view the various parts of the preferred embodiment of the invention shown in FIG. 2, and their relationship to one another.

FIG. 4 shows, by enlargement, clearer detail of the distal portion of instrument 10 as seen in FIG. 2.

FIGS. 5A-E depict in further detail the structure of one preferred embodiment of the distal end of surgical tip 38. FIG. 5A shows in perspective the radially-disposed irrigation ports 50a, b, c, and d, and their relationship to aspiration port 48. It also shows the relationship of Aspiration cannula 46 to the hollow interior 44 of surgical tip 48.

Figure 5B:
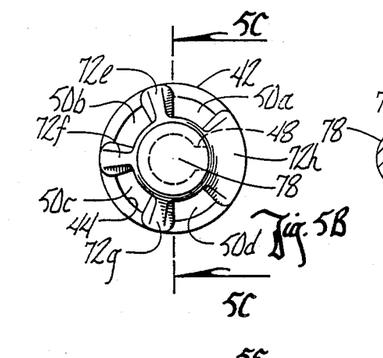
FIG. 5B is a distal end view of FIG. 5A.

FIG. 5B shows an end or anterior view of distal end 42 of surgical tip 38, and how in the preferred embodiment a port-free solid portion 72h of wider dimensions than solid portions 72e, f, and g, exists between irrigation ports 50a and 50d in alignment with and proximal to aspiration port 48. The reason for wider solid portion 72h is to allow constant irrigation without dislodging or washing away the material immediately forward of and coaxial to aspiration port 48.

In the preferred embodiment of FIGS. 5A-E, wider solid portion 72h consists of a pre-shaped solid area comprising generally a 40° arc segment of the generally conical shape of slanted portion 76. The 40° segment is composed of segments of approximately 20° from either side of a centerline on portion 72h extending to aspiration port 48. Portion 72h generally should be wider than the irrigation ports.

Figure 5C:
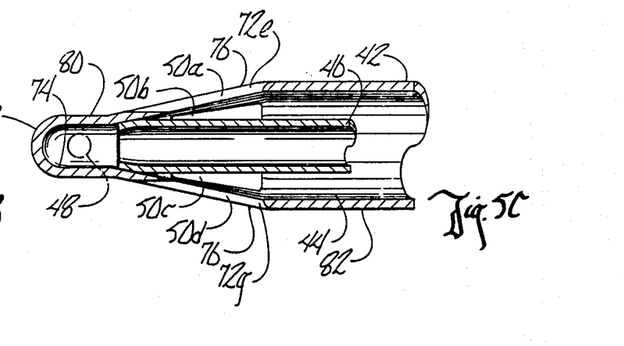
FIG. 5C is a sectional view taken along lines 5C—5C of FIG. 5B.
Figure 6B:
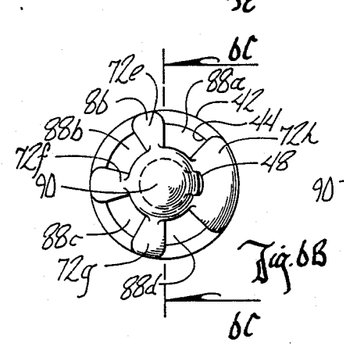
FIG. 6B is a distal end view of FIG. 6A.
Figure 6C:
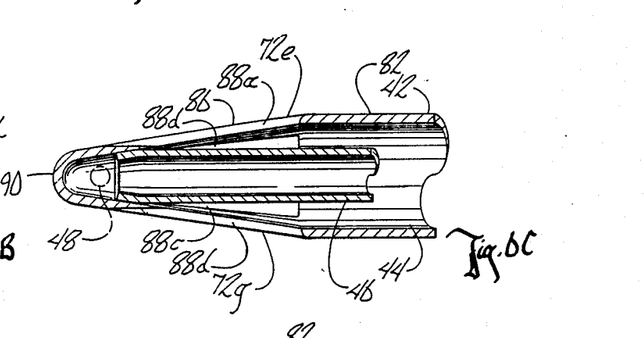
FIG. 6C is a sectional view taken along lines 6C—6C of FIG. 6B.
Figure 6D:
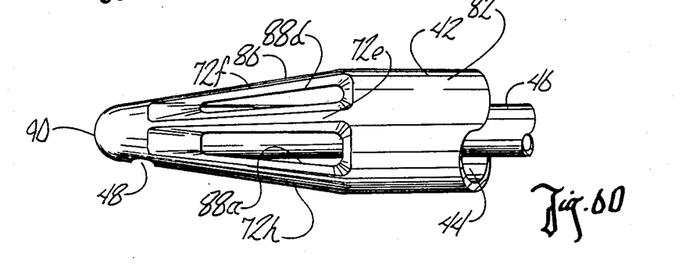
FIG. 6D is a top view of FIG. 6A.

FIG. 5C depicts in greater detail how aspiration cannula 46 can be force fit and secured into narrowed interior portion 74 of surgical tip 38. Aspiration cannula 46 can be of a deformable yet resilient material which allows such securing force fit. Alternative methods of securing aspiration cannula 46 can be used, such as are known in the art. It can be seen that aspiration cannula 46 does not disrupt the flow of irrigation fluid from hollow interior 44 of surgical tip 38 and out of the plurality of irrigation ports 50a-d.

Figure 5D:
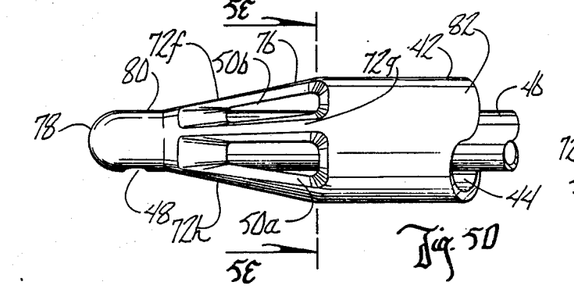
FIG. 5D is a top view of FIG. 5A.

FIG. 5D shows a side view of aspiration port 48 and its relationship to the slanted portion 76 which is intermediate between grounded closed end 78 and narrowed straight portion 80 of surgical tip 38, and the straight sided connection portion 82 of surgical tip 38 which extends back to the proximal end 40 of surgical tip 38.

Figure 5E:
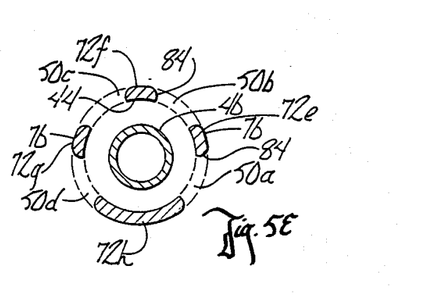
FIG. 5E is a sectional view taken along lines 5E—5E of FIG. 5D.

FIG. 5E shows how in the preferred embodiment, the edges of irrigation ports 50a-d and aspiration port 48 can be rounded to prevent any catching or tearing at the surgical site.

FIGS. 6A-D depict an alternative embodiment for the distal end of the surgical tip. It functions in exactly the same manner as surgical tip 38 in FIGS. 1 through 5, except that it differs in that it has tapered portion 86 which extends from just proximally behind irrigation ports 88a-d, all the way to rounded closed end 90. Thus, for purposes of comparison, the preferred embodiment of FIGS. 5A-E can have slanted portion 76 at an angle of approximately 12° spread from the center longitudinal axis of surgical tip 38, whereas the embodiment of FIGS. 6A-D would have a spread angle of approximately 9° from the longitudinal axis. The embodiment of FIGS. 6A-D thus presents somewhat of a shallower angle.

FIG. 7 shows end plug 54 and strain plug 56 in position in handle 12. It can be seen that apertures 58, 60 of end plug 54 are adjacent and are radially centered from the center of end plug 54. Apertures 62, 64 of strain plug 56 are likewise adjacent and centered from the center of strain plug 56. However, to provide the strain relief, apertures 62, 64 are offset rotationally from apertures 58, 60. In the preferred embodiment, this offset is approximately 30°.

FIG. 8 shows how the offset creates a bend 92 in aspiration conduit 20 which assists in securing conduit 20 in place and also provides strain relief. The same effect is caused on irrigation conduit 22.

Thus, the present invention provides reliable and segregated, but simultaneous irrigation and aspiration. It is also important to note that handpiece 10 also provides an irrigation fluid reservoir, which facilitates consistent and constant irrigation, with the plurality of radially spaced irrigation ports providing further advantageous irrigation, which is more complete and less turbulent than prior aspiration irrigation handpieces which generally utilize two irrigation ports on opposite sides of the irrigation cannula.

The different embodiments of the surgical tips highlight the advantage of the present invention in that the entire surgical tip has no interruptions, junctions, joints, or protrusions, and that all surfaces are gradually slanted or rounded. The surgical tip is essentially unitary, which is advantageous for clean wound penetration. Conventional instruments are fabricated by coaxially aligning two cannulas which, of necessity, requires a joint or junction or some interruption in the surface. Even the smallest interruption can cause tearing or tissue damage.

It will be appreciated that the present invention can take many forms and embodiments. The true essence and spirit of this invention are defined in the appended claims, and it is not intended that the embodiment of the invention presented herein should limit the scope thereof.

What is claimed is:

1. An improved apparatus for supplying fluid to and withdrawing fluid from a surgical site, said apparatus comprising:

a handle member having distal and proximal ends, an intermediate body section, and a bore therethrough;

a nose chamber means having a proximal end in fluid communication with the distal end of the handle member, an enclosed hollow interior means forming an irrigation fluid reservoir substantially across the interior cross-sectional width and through a substantial portion of the longitudinal length of the nose chamber means, and a distal end extending outwardly from the distal end of the handle member;

a surgical tip means having a housing defining a hollow interior of smaller cross-sectional width than the hollow interior means of the nose chamber means in fluid communication with the reservoir of the nose chamber, a proximal end open for direct, unobstructed fluid communication with the fluid reservoir at the distal end of the nose chamber means, and a distal end extended away from the distal end of the nose chamber means, the housing of the tip means having a unitary uninterrupted outer surface extending from the proximal end and including the distal end, which is enclosed, the surface including only smooth, rounded portions without any joints, junctions, exposed projections, and interruptions related to any other parts of the apparatus;

irrigation fluid outlet means and aspiration inlet means both positioned at the distal end of the tip means adjacent to the enclosed, rounded distal end, facilitating fluid communication with the exterior of the distal end of the surgical tip means, the irrigation fluid outlet means comprising a plurality of outlet ports at or near the distal end of the surgical tip means and distributed at generally equally spaced apart positions radially about the longitudinal axis of the surgical tip means with solid portions of the housing separating the irrigation ports, except for a blocking solid portion, substantially wider than the solid portions, positioned immediately longitudinally adjacent the aspiration inlet means between the aspiration inlet means and any outlet ports of the irrigation fluid outlet means, the outlet ports of the irrigation fluid outlet means allowing increased and improved irrigation around a majority of the radial perimeter of the tip means, the blocking solid portion blocking irrigation fluid from being directly oriented towards the aspiration inlet means and from creating interference with aspiration of the apparatus, the irrigation outlet ports and the aspiration inlet means having smooth, rounded edges without exposed and raised joints, junctions and interruptions;

irrigation fluid conduit means extending through said proximal end, body section, and distal end of the handle member for supplying irrigation fluid to the fluid reservoir of the nose chamber means, irrigation fluids to the irrigation fluid outlet means being supplied through the hollow interiors of the nose chamber means and the surgical tip means;

aspiration fluid conduit means extending from the proximal end of the nose chamber through the body section to the proximal end of the handle member for conducting aspirated fluid and materials out of the proximal end of the handle member;

an aspiration fluid cannula means being entirely enclosed in and extending from the distal end of the surgical tip means, through the hollow interior of the surgical tip means and the nose chamber means for transferring aspirated fluid between the aspiration inlet means and the aspiration fluid conduit means, the aspiration fluid cannula means having an end opening in stationary sealed fluid communication with the aspiration inlet means at the distal end of the surgical tip means.

2. The apparatus of claim 1 wherein the handle member includes a hollow interior with distal and proximal ends being open to the hollow interior.

3. The apparatus of claim 1 wherein the nose chamber means is comprised of a separate piece from that of the handle member, and is sealingly secured thereto.

4. The apparatus of claim 1 wherein the irrigation and aspiration fluid conduits are separate tube means.

5. The apparatus of claim 4 wherein the irrigation fluid conduit is connected in fluid communication to an irrigation fluid source, and the aspiration fluid conduit is connected in fluid communication to an aspiration source.

6. The apparatus of claim 4 wherein the proximal end of the handle member includes an end plug having first and second apertures through which extend the separate tube means for the irrigation and aspiration fluid conduits to enter the handle member.

7. The apparatus of claim 6 wherein the separate tube means are elastomeric and frictionally fit within the first and second apertures of the end plug.

8. The apparatus of claim 7 further comprising a strain plug mounted inwardly in the handle member from the end plug and having first and second apertures through which the separate tube means pass from outside of and into the handle member, said first and second apertures of the strain plug being offset from the first and second apertures of the end plug to provide strain relief for the separate tube means.

9. The apparatus of claim 4 wherein the nose chamber means includes at its proximal end a chamber bulkhead having a first connection means for the tube means of the irrigation fluid conduit to communicate irrigation fluid between the irrigation fluid conduit and the reservoir of the nose chamber, and a second connection means for the tube means of the aspiration fluid conduit for communicating the aspiration fluid conduit with the aspiration fluid cannula means.

10. The apparatus of claim 1 wherein the surgical tip means has a unitary, uniform outer surface to provide an uninterrupted surface to the surgical site.

11. The apparatus of claim 10 wherein the surgical tip means has a longitudinal axis, a closed tip end, a tapered section extending from the tip end, and a cannula section extending from the tapered section towards the proximal end of the surgical tip.

12. The apparatus of claim 1 wherein the aspiration inlet means comprises an aperture at or near the distal end of the surgical tip means and is in fluid communication with the aspiration fluid cannula.

13. The apparatus of claim 1 wherein the surgical tip means includes a tapered section between its distal end and its proximal end.

14. The apparatus of claim 1 wherein the distal end of the surgical tip means includes a front section which is narrower in cross section than a back section in fluid communication with the proximal end of the surgical tip means, and which further comprises a closed tip end.

15. A surgical tip for use with an apparatus for supplying fluid to and withdrawing fluid from a surgical site, comprising:

irrigation cannula means comprising a generally tubular housing having a generally smooth unitary outer surface without any joints, and sharp and exposed projections and extending from an open proximal end in fluid communication with the apparatus, an enclosed and rounded distal end, and a hollow interior passageway, and including at least one irrigation port in the housing facilitating fluid communication with the exterior of the distal end of the irrigation cannula means, and supplying irrigation fluid between the interior passageway and the exterior of the irrigation port, the distal end of said irrigation cannula means also including an aspiration port in the housing, the irrigation and aspiration ports having smooth, rounded edges;

aspiration cannula means having a proximal end in fluid communication with the apparatus, and extending through the interior passageway of the irrigation cannula means to a distal end which is in fluid communication with the aspiration port but entirely enclosed within the housing of the irrigation cannula means to communicate the exterior of the aspiration port with the apparatus;

the irrigation cannula means having a longitudinal axis, and including an end tip section extending from the distal end of the irrigation cannula means inwardly, a connecting section extending from the proximal end of the irrigation cannula means towards the end tip section, and an intermediate section between the end tip section and the connecting section;

the intermediate section including the at least one irrigation port; and the at least one irrigation port being positioned radially around the intermediate section with solid portions of the housing between each irrigation port, the solid portions of the housing including a blocking solid portion positioned immediately longitudinal adjacent the aspiration port in the tip section between the aspiration port and any irrigation outlet ports, the irrigation outlet ports allowing increased and improved irrigation around a majority of the radial perimeter of the tip, the blocking solid portion blocking irrigation fluid from being directly oriented towards the aspiration port and from creating interference with aspiration of the apparatus.

16. The tip of claim 15 wherein the end tip section includes the aspiration port.

17. The tip of claim 15 wherein the intermediate section is tapered towards the end tip and is generally conical in shape.

18. The tip of claim 15 wherein the irrigation ports are radially spaced around the longitudinal axis of the intermediate section.

19. The tip of claim 15 wherein the aspiration port is positioned on a side of the end tip section.

20. The tip of claim 15 wherein a solid portion of the housing is positioned between the adjacent irrigation ports immediately above the aspiration port and comprises an arcuate segment of the general conical intermediate section of approximately 40° of the circumference of the intermediate section of the housing.

21. The tip of claim 20 wherein four irrigation ports are distributed around the remaining 320° of the intermediate section circumference of the housing.

22. The tip of claim 15 wherein the interior of the end tip section is narrower in diameter than the other sections of the surgical tip means.

23. The tip of claim 22 wherein the aspiration cannula is sealingly secured into the interior of the end tip section.

24. The tip of claim 21 wherein the aspiration cannula is force fit into the interior of the end tip section.

25. The apparatus of claim 15 wherein irrigation and aspiration ports have outer rounded edge surfaces.

26. The apparatus of claim 1 further comprising indicia means on the apparatus for visual and tactile orientation of the position of the aspiration port.

27. An improved apparatus for supplying fluid to and withdrawing fluid from a surgical site, said apparatus comprising:

a handle member having distal and proximal ends, an intermediate body section, and a bore therethrough;

a nose chamber means having a proximal end in fluid communication with the distal end of the handle member, an enclosed hollow interior means forming an irrigation fluid reservoir substantially across the interior cross-sectional width and through a substantial portion of the longitudinal length of the nose chamber means, and a distal end extending outwardly from the distal end of the handle member;

a surgical tip means having a housing defining a hollow interior of smaller cross-sectional width than the hollow interior means of the nose chamber means in fluid communication with the reservoir of the nose chamber, a proximal end open for direct, unobstructed fluid communication with the fluid reservoir at the distal end of the nose chamber means, and a distal end extended away from the distal end of the nose chamber means, the housing of the tip means having a unitary uninterrupted outer surface extending from the proximal end and including the distal end, which is enclosed, the surface including only smooth, rounded portions without any joints, junctions, exposed projections, and interruptions related to any other part of the apparatus;

irrigation fluid outlet means and aspiration inlet means facilitating fluid communication with the exterior of the distal end of the surgical tip means, the irrigation fluid outlet means comprising a plurality of outlet ports at or near the distal end of the surgical tip means and distributed at generally equally spaced apart positions radially about the longitudinal axis of the surgical tip means with solid portions of the housing separating the irrigation ports, except for a blocking solid portion substantially wider than the solid portions positioned immediately longitudinally adjacent the aspiration inlet means between the aspiration inlet means and any outlet ports of the irrigation fluid outlet means, the outlet ports of the irrigation fluid outlet means allowing increased and improved irrigation around a majority of the radial perimeter of the tip means, the blocking solid portion blocking irrigation fluid from being directly oriented towards the aspiration inlet means and from creating interference with aspiration of the apparatus, the irrigation outlet ports and the aspiration inlet means having smooth, rounded edges without exposed and raised joints, junctions and interruptions;

irrigation fluid conduit means extending through said proximal end, body section, and distal end of the handle member for supplying irrigation fluid to the fluid reservoir of the nose chamber means, irrigation fluids to the irrigation fluid outlet means being supplied through the hollow interiors of the nose chamber means and the surgical tip means;

aspiration fluid conduit means extending from the proximal end of the nose chamber through the body section to the proximal end of the handle member for conducting aspirated fluid and materials out of the proximal end of the handle member;

an aspiration fluid cannula means being entirely enclosed in and extending from the distal end of the surgical tip means through the hollow interior of the surgical tip means and the nose chamber means for transferring aspirated fluid between the aspiration inlet means and the aspiration fluid conduit means, the aspiration fluid cannula means having an end opening in sealed fluid communication with the aspiration inlet means at the distal end of surgical tip means;

the irrigation and aspiration fluid conduits comprising separate tube means; and the nose chamber means including at its proximal end a chamber bulkhead having a first connection means for the tube means of the irrigation fluid conduit to communicate irrigation fluid between the irrigation fluid conduit and the reservoir of the nose chamber, and a second connection means for the tube means of the aspiration fluid conduit for communicating the aspiration fluid conduit means with the aspiration fluid cannula means.

28. A surgical tip for use with an apparatus for supplying fluid to and withdrawing fluid from a surgical site, comprising irrigation cannula means comprising a generally tubular housing having a generally smooth unitary outer surface without any joints, and sharp and exposed projections, extending from an open proximal end in fluid communication with the apparatus, an enclosed and rounded distal end, and a hollow interior passageway, and including at least one irrigation port in the housing facilitating fluid communication with the exterior of the distal end of the irrigation cannula means, and supplying irrigation fluid between the interior passageway and the exterior of the irrigation port, the distal end of said irrigation cannula means also including an aspiration port in the housing, the irrigation and aspiration ports having smooth, rounded edges;

aspiration cannula means having a proximal end in fluid communication with the apparatus, and extending through the interior passageway of the irrigation cannula means to a distal end which is in fluid communication with the aspiration port but entirely enclosed within the irrigation cannula to communicate the exterior of the aspiration port with the apparatus;

the irrigation cannula having a longitudinal axis, and including an end tip section extending from the distal end of the irrigation cannula inwardly, a connecting section extending from the proximal end of the irrigation cannula means towards the end tip section, and an intermediate section between the end tip section and the connecting section;

the intermediate section including a plurality of three or more irrigation ports;

the irrigation ports being positioned radially around the intermediate section with solid portions of the housing between irrigation ports, the solid portions of the housing including a blocking solid portion positioned immediately adjacent the aspiration port in the tip section between the aspiration inlet means and any outlet ports of the irrigation fluid outlet means, the outlet ports of the irrigation fluid outlet means allowing increased and improved irrigation around a majority of the radial perimeter of the tip, the blocking solid portion blocking irrigation fluid from being directly oriented towards tho aspiration inlet means and from creating interference with aspiration of the apparatus; and the blocking solid portion of the housing comprising an arcuate segment of the generally conical intermediate section of approximately 40 of the circumference of the intermediate section of the housing, the irrigation ports being distributed around the remaining 320 of the intermediate section circumference of the housing.

29. An improved apparatus for supplying fluid to and withdrawing fluid from a surgical site, said apparatus comprising:

a handle member having distal and proximal ends, an intermediate body section, and a bore therethrough;

a nose chamber means having a proximal end in fluid communication with the distal end of the handle member, an enclosed hollow interior means forming an irrigation fluid reservoir substantially across the interior cross-sectional width and through a substantial portion of the longitudinal length of the nose chamber means, and a distal end extending outwardly from the distal end of the handle member;

a surgical tip means having a housing defining a hollow interior of a smaller cross-sectional width than the hollow interior means of the nose chamber means in fluid communication with the reservoir of the nose chamber, a proximal end open for direct, unobstructed fluid communication with the fluid reservoir at the distal end of the nose chamber means, and a distal end extended away from the distal end of the nose chamber means, the housing of the tip means having a unitary uninterrupted outer surface extending from the proximal end and including the distal end, which is enclosed and rounded, the surface including only smooth, rounded portions without any joints, junctions, exposed projections, and interruptions related to any other part of the apparatus;

irrigation fluid outlet means and aspiration inlet means, both positioned at the distal end of the tip means adjacent to the enclosed, rounded distal end, facilitating fluid communication with the exterior of the distal end of the surgical tip means, the irrigation fluid outlet means comprising a plurality of outlet ports at or near the distal end of the surgical tip means and distributed at generally equally spaced apart positions radially about the longitudinal axis of the surgical tip means with solid portions of the housing separating the irrigation ports, except for a blocking solid portion substantially wider than the solid portions positioned immediately adjacent the aspiration inlet means between the aspiration inlet means and any outlet ports of the irrigation fluid outlet means, the outlet ports of the irrigation fluid outlet means allowing increased and improved irrigation around a majority of the radial perimeter of the tip means, the blocking solid portion blocking irrigation fluid from being directly oriented towards the aspiration inlet means and from creating interference with aspiration of the apparatus, the irrigation outlet ports and the aspiration inlet means having smooth, rounded edges without exposed and raised joints, junctions and interruptions;

irrigation fluid conduit means extending through said proximal end, body section, and distal end of the handle member for supplying irrigation fluid to the fluid reservoir of the nose chamber means, irrigation fluids to the irrigation fluid outlet means being supplied through the hollow interiors of the nose chamber means and the surgical tip means;

aspiration fluid conduit means extending from the proximal end of the nose chamber through the body section to the proximal end of the handle member for conducting aspirated fluid and materials out of the proximal end of the handle member;

an aspiration fluid cannula means being entirely enclosed in and extending from the distal end of the surgical tip means through the hollow interior of the surgical tip means and the nose chamber means for transferring aspirated fluid between the aspiration inlet means and the aspiration fluid conduit means, the aspiration fluid cannula means having an end opening in sealed fluid communication with the aspiration inlet means at the distal end of surgical tip means;

the irrigation and aspiration fluid conduits being separate tube means;

the proximal end of the handle member including an end plug having first and second apertures through which extend the separate tube means for the irrigation and aspiration fluid conduits to enter the handle member; and the separate tube means being elastomeric and frictionally fit within the first and second apertures of the end plug.

30. A surgical tip for use with an apparatus for supplying fluid to and withdrawing fluid from a surgical site, comprising:

irrigation cannula means comprising a generally tubular housing having a generally smooth unitary outer surface without any joints and sharp and exposed projections, extending from an open proximal end in fluid communication with the apparatus, an enclosed and rounded distal end, and a hollow interior passageway, and including at least one irrigation port in the housing facilitating fluid communication with the exterior of the distal end of the irrigation cannula means, and supplying irrigation fluid between the interior passageway and the exterior of the irrigation port, the distal end of said irrigation cannula means also including an aspiration port in the housing, the irrigation and aspiration ports having smooth, rounded edges;

aspiration cannula means having a proximal end in fluid communication with the apparatus, and extending through the interior passageway of the irrigation cannula means to a distal end which is in fluid communication with the aspiration port but entirely enclosed within the irrigation cannula means to communicate the exterior of the aspiration port with the apparatus;

the irrigation cannula means having a longitudinal axis, and including an end tip section extending form the distal end of the irrigation cannula means inwardly, a connecting section extending from the proximal end of the irrigation cannula means towards the end tip section, and an intermediate section between the end tip section and the connecting section;

the intermediate section including at least three or more irrigation ports;

the irrigation ports being positioned radially around the intermediate section with solid portions of the housing between irrigation ports, the solid portions of the housing including a blocking solid portion positioned immediately adjacent the aspiration port in the tip section between the aspiration inlet means and any outlet ports of the irrigation fluid outlet means, the outlet ports of the irrigation fluid outlet means allowing increased and improved irrigation around a majority of the radial perimeter of the tip means, the blocking solid portion blocking irrigation fluid from being directly oriented towards the aspiration inlet means and from creating interference with aspiration of the apparatus;

the blocking solid portion of the housing comprising an arcuate segment of the generally conical intermediate section of approximately 40 of the circumference of the intermediate section of the housing, the irrigation ports being distributed around the remaining 320 of the circumference of the intermediate section; and the aspiration cannula being force fit into the interior of the end tip section of the irrigation cannula means.

* * * * *